US012781182B2

(12) United States Patent
Han et al.

(10) Patent No.: US 12,781,182 B2
(45) Date of Patent: Nov. 3, 2026

(54) ***BACILLUS SUBTILIS* FNFH_BS08 AND USE THEREOF**

(71) Applicant: ZHEJIANG OCEAN UNIVERSITY, Zhejiang (CN)

(72) Inventors: Tao Han, Zhejiang (CN); Yan Chen, Zhejiang (CN); Jiteng Wang, Zhejiang (CN); Yunping Tang, Zhejiang (CN); Jialang Zheng, Zhejiang (CN); Fangmiao Yu, Zhejiang (CN); Zuisu Yang, Zhejiang (CN)

(73) Assignee: ZHEJIANG OCEAN UNIVERSITY, Zhejiang (CN)

( * ) Notice: Subject to any disclaimer, the term of this patent is extended or adjusted under 35 U.S.C. 154(b) by 349 days.

(21) Appl. No.: 18/555,540

(22) PCT Filed: May 24, 2023

(86) PCT No.: PCT/CN2023/095949

§ 371 (c)(1),
(2) Date: Oct. 16, 2023

(87) PCT Pub. No.: WO2023/231854

PCT Pub. Date: Dec. 7, 2023

(65) Prior Publication Data

US 2025/0075169 A1 Mar. 6, 2025

(30) Foreign Application Priority Data

Jun. 2, 2022 (CN) ......................... 202210619567.1

(51) Int. Cl.

| | |
|---|---|
| ***C12N 1/20*** | (2026.01) |
| ***A23K 10/12*** | (2016.01) |
| ***C12R 1/125*** | (2006.01) |

(52) U.S. Cl.

CPC ................ *C12N 1/20* (2013.01); *A23K 10/12* (2016.05); *C12R 2001/125* (2021.05)

(58) Field of Classification Search

CPC ...... C12N 1/20; C12N 1/205; C12R 2001/125
See application file for complete search history.

(56) References Cited

U.S. PATENT DOCUMENTS

2008/0044501 A1 2/2008 Lee et al.

FOREIGN PATENT DOCUMENTS

| | | | |
|---|---|---|---|
| CN | 106167782 | 11/2016 | |
| CN | 106167782 A * | 11/2016 | ............. C12N 1/205 |

(Continued)

OTHER PUBLICATIONS

Ramos et al. "Fermentative Metabolism of Bacillus subtilis: Physiology and Regulation of Gene Expression", Jun. 2000, Journal of Bacteriology, vol. 182, No. 11, p. 3072-3080. (Year: 2000).*

(Continued)

*Primary Examiner* — Samira J Jean-Louis
*Assistant Examiner* — Amelia Nicole Dickens
(74) *Attorney, Agent, or Firm* — JCIPRNET

(57) ABSTRACT

The present invention belongs to the technical field of microorganisms, and provides a *Bacillus subtilis* FNFH_BS08 and use thereof. On the one hand, the present invention provides a *Bacillus subtilis* FNFH_BS08, on the other hand, the present invention provides use of the *Bacillus subtilis* FNFH_BS08. The *Bacillus subtilis* FNFH_BS08 of the present invention can efficiently degrade main antigen proteins and non-starch polysaccharides in soybean meal by secreting highly active carbohydrate enzymes and proteases, thus improving the overall nutritional parameters of the soybean meal, improving the nutritional value of the soy- (Continued)

bean meal, and reaching a leading level in the field of fermentation of soybean meal by microorganisms.

5 Claims, 4 Drawing Sheets

Specification includes a Sequence Listing.

(56) References Cited

FOREIGN PATENT DOCUMENTS

| | | | | |
|---|---|---|---|---|
| CN | 109207390 | | 1/2019 | |
| CN | 111826295 | | 10/2020 | |
| CN | 112795504 | | 5/2021 | |
| CN | 113073058 | | 7/2021 | |
| CN | 115197876 | | 10/2022 | |
| WO | WO-2023231853 A1 | * | 12/2023 | ............ C07K 14/32 |

OTHER PUBLICATIONS

English machine translation of WO 2023231853 A1 (Year: 2023).*

CN 202210619560, priority document for WO 2023231853 A1 (Year: 2022).*

English machine translation of CN-106167782-A (Year: 2016).*

Tao Xiong et al., "Screening and identification of protease-producing bacteria with acid-resistance and the preliminary trial of soybean meal fermented by multi-microorganism", Food and Fermentation Industries, Aug. 31, 2013, with English abstract, pp. 96-101, vol. 39, No. 8, Abstract only.

Shifei Liu, "Bacillus subtilis strain XZ18-3 16S ribosomal RNA gene, partial sequence", GenBank: MK721058.1, Apr. 7, 2019, pp. 1-2, available at: https://www.ncbi.nlm.nih.gov/nuccore/1604999224.

P. B. Agbobatinkpo et al. "Bacillus subtilis strain Y98b DNA gyrase subunit B (gyrB) gene, partial cds", GenBank: JX513934.1, Apr. 20, 2013, pp. 1-2, available at: https://www.ncbi.nlm.nih.gov/nuccore/JX513934.

Shuo Gao et al., "Screening of bacterial strains from the gut of Pacific White Shrimp (*Litopenaeus vannamei*) and their efficiencies in improving the fermentation of soybean meal", FEMS Microbiology Letters, Feb. 3, 2020, pp. 1-10, vol. 367, No. 2.

Yang Li et al., "Isolation of a Highly Efficient Antigenic-Protein-Degrading Bacillus amyloliquefaciens and Assessment of Its Safety", Animals, Jul. 6, 2020, pp. 1-15, vol. 10, No. 1144.

* cited by examiner

Lane:
M: protein molecular protein standard
1: soybean meal
2: FNFH_BS08 fermented soybean meal
3: FNFH_BS08 fermented soybean meal

*BACILLUS SUBTILIS* FNFH_BS08 AND USE THEREOF

CROSS-REFERENCE TO RELATED APPLICATION

This application is a 371 of international application of PCT application serial no. PCT/CN2023/095949, filed on May 24, 2023, which claims the priority benefit of China application no. 202210619567.1, filed on Jun. 2, 2022. The entirety of each of the above-mentioned patent application is hereby incorporated by reference herein and made a part of this specification.

BACKGROUND OF THE INVENTION

1. Technical Field

The present invention belongs to the technical field of microorganisms, and particularly relates to a *Bacillus subtilis* FNFH_BS08 and use thereof.

2. Background Art

China has reached a bottleneck in the production of protein feed resources for the long-term dependence on imports. Now, the gap is increasing year by year, the conflicts among people, livestock, aquatic and food have been a serious threat to the national food security strategy. Where, soybean is one of the most important and scarce protein resources that limits the development of China's feed industry. As the largest vegetable protein feed resource in China, soybean meal features high crude protein content, reasonable amino acid composition and low price. However, there are also a variety of anti-nutritional factors in soybean meal, including a large number of protein allergens, non-starch polysaccharides, trypsin inhibitors, oligosaccharides and urease, which greatly reduce the nutritive value and protein digestibility, and aggravate the shortage of feedstuff resources. Thus, it is urgent and critical to make the most of the protein feed ingredients in soybean meal, so as to stimulate the development of feed industry.

Microbial fermentation of raw soybean meal is considered to occupy an absolute advantage in the pre-treatment effect of feed ingredients, for microbial growth will secrete highly active carbohydrases, proteases and other enzyme systems, which in turn effectively decompose and destroy the anti-nutritional factors in soybean meal. Strain is the core of microbial fermentation, and its quality directly determines the nutritional value of fermented feed. *Bacillus* is considered the "best" choice for fermented soybean meal production because of its rapid growth and strong enzyme production. Gao et al. selected a strain of *Bacillus stratosphericus* that could efficiently secrete protease, cellulase and phytase. After 48 hours of fermentation with this bacterium, the trypsin inhibitors are lowered to 1.06 TUI/mg, while the crude protein content was increased by 5.95%, with the major macromolecular proteins reduced to less than 20 kDa (Gao et al., 2020). By plate screening, Li Yang et al. selected a strain of *Bacillus amyloliquefaciens* that could secrete 18 hydrolases for degradation. After 24 hours of fermentation with this bacterium, 92.32% glycinin and 85.05% β-conglycinin in soybean meal were degraded, while the content of acid-soluble proteins and essential amino acids were significantly improved (Li et al., 2020). At present, the quality of fermented soybean meal in the domestic market varies, and the performance of fermented strains directly determines whether soybean meal is fermented thoroughly and its nutritional value. Therefore, the development of high-quality and efficient strains for soybean meal fermentation is fundamental to realize the value-added utilization of the protein sources in soybean meal.

SUMMARY OF THE INVENTION

The present invention aims to design a technical solution for providing a *Bacillus subtilis* FNFH_BS08 and use thereof in response to the problems existing in the prior art.

The present invention is specifically implemented by the following technical solution.

A first aspect of the present invention provides a *Bacillus subtilis* FNFH_BS08. The strain has been preserved in the China General Microbiological Culture Collection Center (CGMCC for short, address: No. 3 Courtyard 1 West Beichen Road, Chaoyang District, Beijing, Institute of Microbiology, Chinese Academy of Sciences) on May 6, 2022, with a preservation number of CGMCC No. 24837.

A second aspect of the present invention provides a bacterial agent containing the *Bacillus subtilis* FNFH_BS08.

A third aspect of the present invention provides a fermented product obtained by fermentation culture of the *Bacillus subtilis* FNFH_BS08.

A fourth aspect of the present invention provides use of the *Bacillus subtilis* FNFH_BS08 or the bacterial agent or the fermented product in efficient degradation of antigen proteins and/or non-starch polysaccharides.

Further, the antigen proteins comprise glycinin and β-conglycinin, and the non-starch polysaccharides comprise cellulose, xylan, mannan, and pectin.

A fifth aspect of the present invention provides use of the *Bacillus subtilis* FNFH_BS08 or the bacterial agent or the fermented product in fermentation of soybean meal.

A fifth aspect of the present invention provides use of the *Bacillus subtilis* FNFH_BS08 or the bacterial agent or the fermented product in improving a nutritional value of soybean meal in fermentation of the soybean meal.

Further, the improving a nutritional value of soybean meal is specifically manifested by a decrease in content of antigen proteins, non-starch polysaccharides, oligosaccharides and a trypsin inhibitor, an increase in content of a crude protein and a water-soluble protein, and an increase in protein solubility in fermented soybean meal.

The *Bacillus subtilis* FNFH_BS08 of the present invention can efficiently degrade main antigen proteins and non-starch polysaccharides in soybean meal by secreting highly active carbohydrate enzymes and proteases, thus improving the overall nutritional parameters of the soybean meal, improving the nutritional value of the soybean meal, and reaching a leading level in the field of fermentation of soybean meal by microorganisms.

DETAILED DESCRIPTION OF THE EMBODIMENTS

Figure 1:
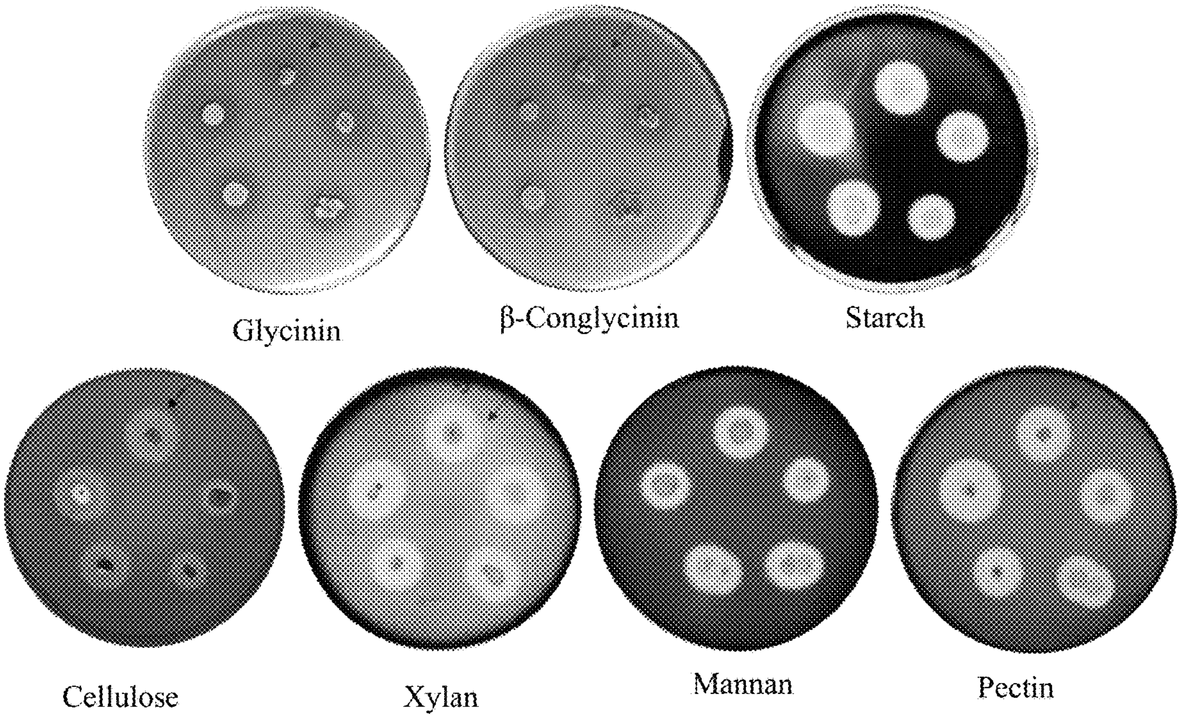
FIG. 1 shows a screening process of a potential advantageous *Bacillus* in fermentation of soybean meal, with arrows pointing to *Bacillus subtilis* FNFH_BS08.

In order to fully disclose a *Bacillus subtilis* strain and use thereof of the present invention, an explanation is given in conjunction with embodiments, but it does not imply any limitation to the present invention.

Embodiment 1: Separation, Screening, and Identification of *Bacillus subtilis* FNFH_BS06

Experimental Materials:

Mediums:

LB medium: 10 g/L peptone, 5 g/L yeast extract, 5 g/L sodium chloride;

Glycinin screening plate: 0.5 g/L glycinin, 2.5 g/L glucose, 0.2 g/L NaCl, 0.5 g/L $K_2HPO_4$, 0.2 g/L $MgSO_4$ $7H_2O$, pH 7.0;

β-Conglycinin screening plate: 0.5 g/L β-conglycinin, 2.5 g/L glucose, 0.2 g/L NaCl, 0.5 g/L $K_2HPO_4$, 0.2 g/L $MgSO_4$ $7H_2O$, pH 7.0.

Experimental Method:

1. Separation and Screening of *Bacillus*

5 g of a fermented soybean sample was taken into a 50 mL centrifuge tube with 40 mL of sterile normal saline, subjected to shake culture in a shaker at 37° C. for 30 minutes and then placed in an 80° C. water bath for processing for 20 minutes. Then, the sample solution was diluted with sterile normal saline in a 10-fold gradient. A suitable dilution of bacterial suspension was taken and coated on an LB solid medium plate, with repeating three times for each dilution. Inverted culture was carried out for 24 hours at a constant temperature of 37° C. After colonies grew, strains with *Bacillus* colony morphological characteristics were selected and subjected to streaking purification.

The separated and purified strains were spot-inoculated onto a glycinin screening plate and a β-conglycinin screening plate, respectively, and subjected to inverted culture for 24 hours at 37° C. Transparent zones around the colonies on the antigen plate mediums were observed, the colony diameter (d) and the transparent zone diameter (D) were measured respectively, and the D/d ratio was calculated. This ratio was used as an evaluation indicator of the ability of the strain to degrade antigen proteins. The single colony with the highest D/d ratio was selected from the streaked plates for LB liquid culture to prepare a glycerol stock, which was stored in an 80° C. refrigerator.

Methods for preparing glycinin and β-conglycinin were as follows: 5 g of soybean meal was weighed and crushed to be sieved with a 60-mesh sieve, 75 mL of a 0.03 M Tris-HCl buffer with pH 8.5 was added, shake extraction was carried out at 30° C. to 50° C. and 200 rpm for 1 hour, a supernatant was taken after centrifugation was carried out at 9000 rpm for 10 minutes, 0.01 M $Na_2SO_3$ was added, the pH was regulated to 6.4 with HCl, precipitation was carried out overnight at 4° C., and centrifugation was carried out at 9000 rpm for 10 minutes to obtain a precipitate, which was glycinin. NaCl was added to the separated supernatant to 0.25 M, the pH was regulated to 4 to 6.0 with HCl, shake was carried out for 30 minutes, centrifugation was carried out at 9000 rpm for 10 minutes for separation to obtain a supernatant, the pH was regulated to 4.8, and centrifugation was carried out at 9000 rpm for 10 minutes to obtain a β-conglycinin precipitate. Finally, the glycinin precipitate and the β-conglycinin precipitate were subjected to vacuum freeze drying to obtain a glycinin freeze-dried powder and a β-conglycinin freeze-dried powder.

2. Identification of *Bacillus*

(1) Gram staining identification

The FNFH_BS06 single colony was taken and coated onto a glass slide, diluted evenly with normal saline, fixed, and subjected to Gram staining.

(2) Physiological and biochemical identification Referring to the traditional methods of bacterial identification, according to the "*Bergey's Manual of Determinative Bacteriology*", the physiological and biochemical characteristics of FNFH_BS06 were detected.

(3) 16S rRNA and gyrB gene sequencing identification

By using modern molecular biology identification techniques, bacterial 16S rRNA sequence identification and *Bacillus* conserved gene gyrB identification were carried out. By using the 16S rRNA universal primers 27F and 1492R of bacteria as amplification primers and by using the genome of the strain FNFH_BS06 as a template, PCR amplification was performed on a 16S rRNA sequence; at the same time, primers were designed to amplify the *Bacillus* conserved gene gyrB, and PCR products were recovered and sequenced.

Experimental Results:

(1) The screening results of the separated strains by using the antigen protein plates are shown in Table 1, where the D/d ratio of *Bacillus* FNFH_BS06 on the glycinin screening plate and the β-conglycinin screening plate is greater than 2.5, showing stronger antigen protein degradation characteristics.

TABLE 1

Screening results of *Bacillus* on antigen plates

| | Glycinin | | | β-Conglycinin | | |
|---|---|---|---|---|---|---|
| Strain number | D (mm) | d (mm) | D/d | D (mm) | d (mm) | D/d |
| FNFH_BS01 | 42.3 | 29.3 | 1.4 | 14.3 | 12.7 | 1.1 |
| FNFH_BS02 | 22.4 | 13.2 | 1.7 | 6.3 | 5.2 | 1.2 |
| FNFH_BS03 | 21.3 | 11.4 | 1.9 | 15.2 | 8.9 | 1.7 |
| FNFH_BS04 | 17.6 | 9.2 | 1.9 | 11.7 | 10.2 | 1.1 |
| FNFH_BS05 | 10.7 | 8.1 | 1.3 | 11.3 | 10.5 | 1.1 |
| FNFH_BS06 | 30.1 | 10.2 | 3.0 | 37.2 | 14.4 | 2.6 |

(2) The colony of *Bacillus* FNFH_BS06 is dirty white, opaque and nearly circular, has a moist surface and contains mucus. The Gram staining result is a Gram-positive bacterium, with a rod-shaped body, arranged in single or paired or chain shapes, and with central spores.

(3) Physiological and biochemical detection

*Bacillus* FNFH_BS06 is positive for V-P test and positive for catalase test, can decompose glucose to produce acid, can decompose L-arabinose, cellobiose, D-xylose, sucrose, fructose, maltose, glycerol, D-turanose, mannitol, and sorbitol, and has tolerance to a 7% sodium chloride solution.

(4) The 16S rRNA sequencing results of the *Bacillus* FNFH_BS06 are shown in the sequence list SEQ ID No. 1. BLAST homology comparison was performed on NCBI. The results show that the sequence homology of 16S rDNA between FNFH_BS06 and strains such as *Bacillus subtilis, Bacillus amyloliquefaciens*, and

*Bacillus cereus* reaches 100%. The *Bacillus* conserved gene gyrB sequencing results of FNFH_BS06 are shown in the sequence list SEQ ID No. 2. The BLAST homology comparison results show that the homology between FNFH_BS06 and three strains of *Bacillus subtilis* species reaches 99.4%. In summary, FNFH_BS06 is identified as *Bacillus subtilis*.

Meanwhile, the FNFH_BS06 strain has been preserved in the China General Microbiological Culture Collection Center (CGMCC for short, address: No. 3 Courtyard 1 West Beichen Road, Chaoyang District, Beijing, Institute of Microbiology, Chinese Academy of Sciences) on May 6, 2022, with a preservation number of CGMCC No. 24836.

Embodiment 2: Mutagenesis, Screening, and Characterization of *Bacillus subtilis* FNFH_BS08

Experimental Materials:

Mediums:

LB medium: 10 g/L peptone, 5 g/L yeast extract, 5 g/L sodium chloride;

Glycinin screening plate: 0.5 g/L glycinin, 2.5 g/L glucose, 0.2 g/L NaCl, 0.5 g/L $K_2HPO_4$, 0.2 g/L $MgSO_4$ $7H_2O$, 1.5% agar powder, pH 7.0;

β-Conglycinin screening plate: 0.5 g/L β-conglycinin, 2.5 g/L glucose, 0.2 g/L NaCl, 0.5 g/L $K_2HPO_4$, 0.2 g/L $MgSO_4$ $7H_2O$, 1.5% agar powder, pH 7.0;

Starch screening plate: 10 g/L peptone, 5 g/L sodium chloride, 5 g/L starch, 1.5% agar powder, pH 7.0;

Cellulose screening plate: 10 g/L sodium carboxymethyl cellulose, 10 g/L peptone, 5 g/L sodium citrate, 2 g/L dipotassium hydrogen phosphate, 2 g/L NaAc, 0.2 g/L magnesium sulfate, 0.05 g/L manganese sulfate, 1.5% agar powder, pH 7.0;

Xylan screening plate: 5 g/L xylan, 3 g/L yeast extract, 1 g/L dipotassium hydrogen phosphate, 5 g/L sodium chloride, 1 g/L calcium chloride, 0.01 g/L ferrous sulfate, 1.5% agar powder, pH 7.0;

Mannan screening plate: 5 g/L locust bean gum, 2 g/L dipotassium hydrogen phosphate, 0.2 g/L magnesium sulfate, 2 g/L ammonium chloride, 3 g/L yeast extract, 1.5% agar powder, pH 7.0;

Pectin screening plate: 5 g/L pectin, 3 g/L yeast extract, 0.5 g/L magnesium sulfate, 1 g/L dipotassium hydrogen phosphate, 0.01 g/L ferrous sulfate, 1.5% agar powder, pH 7.0.

Experimental Method:

1. Mutagenesis and Screening of *Bacillus subtilis*

The *Bacillus subtilis* FNFH_BS06, as an original strain, was inoculated into an LB liquid medium, cultured at 37° C. and 250 rpm until the logarithmic growth phase, and centrifuged to collect a bacterial cell, which was washed twice with a PBS buffer and then resuspended to prepare a bacterial suspension. An appropriate amount of bacterial suspension was evenly coated onto a slide, and placed in a mutagenesis machine by sterile tweezers for ordinary pressure and room temperature plasma mutagenesis at 100 W, 10 SLM and 2 mm for mutagenesis time of 40 seconds (lethal rate of >90%). After the mutagenesis was completed, the slide was loaded into an EP tube containing 1.0 mL of an LB medium. After the bacterial cell was shaken and eluted, an appropriate amount of the bacterial cell was taken and evenly coated on an LB plate, and cultured in a 37° C. constant-temperature incubator until a single colony grew.

After the single colony growing after mutagenesis was subjected to streaking purification, the single colony was spot-inoculated onto a glycinin screening plate, a β-conglycinin screening plate, a cellulose screening plate, a xylan screening plate, a mannan screening plate, a pectin screening plate and a starch screening plate, respectively, and then subjected to inverted culture for 24 hours at 37° C. Transparent zones around the colonies on each plate were observed, the colony diameter (d) and the transparent zone diameter (D) were measured respectively, and the D/d ratio was calculated. This ratio was used as an evaluation indicator of the ability of the strain to degrade different substrates (antigen proteins and non-starch polysaccharides). The single colonies with the optimal D/d ratio were selected from the streaked plates for LB liquid culture to prepare a glycerol stock, which was stored in a −80° C. refrigerator.

Methods for preparing glycinin and β-conglycinin were as follows: 5 g of soybean meal was weighed and crushed to be sieved with a 60-mesh sieve, 75 mL of a 0.03 M Tris-HCl buffer with pH 8.5 was added, shake extraction was carried out at 30° C. to 50° C. and 200 rpm for 1 hour, a supernatant was taken after centrifugation was carried out at 9000 rpm for 10 minutes, 0.01 M $Na_2SO_3$ was added, the pH was regulated to 6.4 with HCl, precipitation was carried out overnight at 4° C., and centrifugation was carried out at 9000 rpm for 10 minutes to obtain a precipitate, which was glycinin. NaCl was added to the separated supernatant to 0.25 M, the pH was regulated to 4 to 6.0 with HCl, shake was carried out for 30 minutes, centrifugation was carried out at 9000 rpm for 10 minutes for separation to obtain a supernatant, the pH was regulated to 4.8, and centrifugation was carried out at 9000 rpm for 10 minutes to obtain a β-conglycinin precipitate. Finally, the glycinin precipitate and the β-conglycinin precipitate were subjected to vacuum freeze drying to obtain a glycinin freeze-dried powder and a β-conglycinin freeze-dried powder. 2. Characterization of *Bacillus subtilis*

(1) Gram Staining

The FNFH_BS08 single colony was taken and coated onto a glass slide, diluted evenly with normal saline, fixed, and subjected to Gram staining.

(2) Growth Curve Determination

The glycerol stock of *Bacillus subtilis* FNFH_BS08 was taken and inoculated onto a 5 mL LB medium and subjected to overnight activation culture at 37° C. and 250 rpm. Then the glycerol stock was transferred to a fresh 30 mL LB medium with $OD_{600}$=0.5 and cultured at 37° C. and 250 rpm, with taking samples at regular intervals to determine the $OD_{600}$ value.

Experimental Results:

(1) After the *Bacillus subtilis* FNFH_BS06 were subjected to ordinary pressure and room temperature plasma mutagenesis, mutant strains were spot-inoculated on screening plates containing different substrates (glycinin, β-conglycinin, cellulose, xylan, mannan, pectin and starch). The ability of the strains to degrade antigen proteins, non-starch polysaccharides and starch in the soybean meal was evaluated according to the D/d ratio. Finally, a strain FNFH_BS08 with the best ability to degrade multiple substrates was selected. The results are shown in Table 2, where the D/d ratio thereof on the antigen proteins (glycinin and β-conglycinin), non-starch polysaccharides (cellulose, xylan, mannan, and pectin) and starch screening plates is greater than 2.5, showing strong degradation characteristics for the antigen proteins, non-starch polysaccharides and the like in the soybean meal. FIG. 1 shows a screening process of *Bacillus subtilis* FNFH_BS08.

TABLE 2

| Plate screening results of *Bacillus subtilis* FNFH_BS08 | | | |
|---|---|---|---|
| Substrate | D (mm) | d (mm) | D/d |
| Glycinin | 28.3 | 10.1 | 2.8 |
| β-Conglycinin | 35.6 | 13.2 | 2.7 |
| Cellulose | 27.6 | 8.9 | 3.1 |
| Xylan | 45.4 | 14.2 | 3.2 |
| Mannan | 48.3 | 19.3 | 2.5 |
| Pectin | 24.5 | 7.2 | 3.4 |
| Starch | 44.5 | 17.1 | 2.6 |

Figure 2:
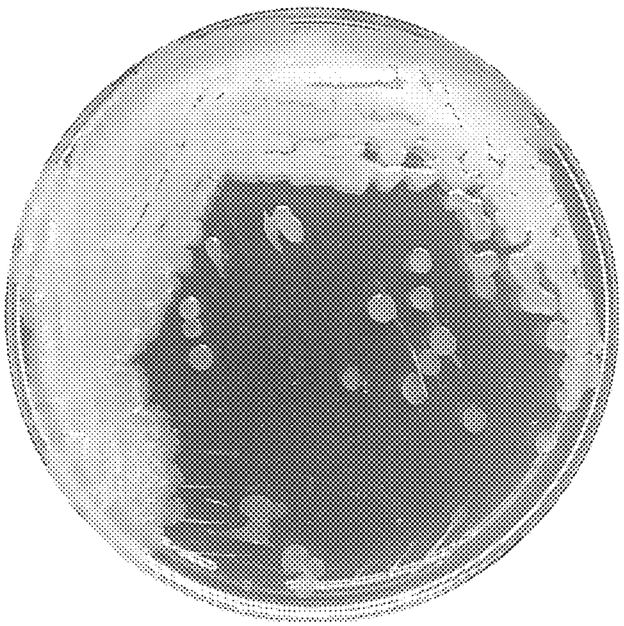
FIG. 2 shows a colony morphology of *Bacillus subtilis* FNFH_BS08.
Figure 3:
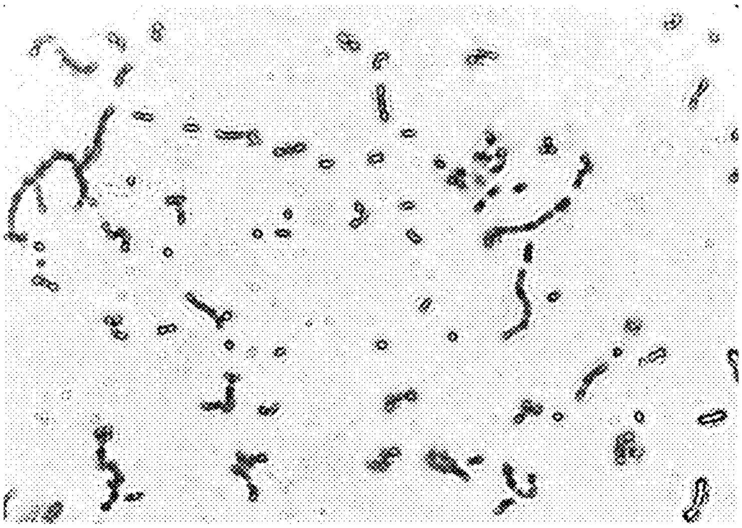
FIG. 3 shows a Gram staining microscopic picture of *Bacillus subtilis* FNFH_BS08.

(2) The colony morphology of *Bacillus* FNFH_BS08 is shown in FIG. 2. The colony is dirty white, opaque and nearly circular, has a moist surface and contains mucus. The Gram staining results are shown in FIG. 3, where FNFH_BS08 is a Gram-positive bacterium, with a rod-shaped body, arranged in single or paired or chain shapes, and with central spores.

Figure 4:
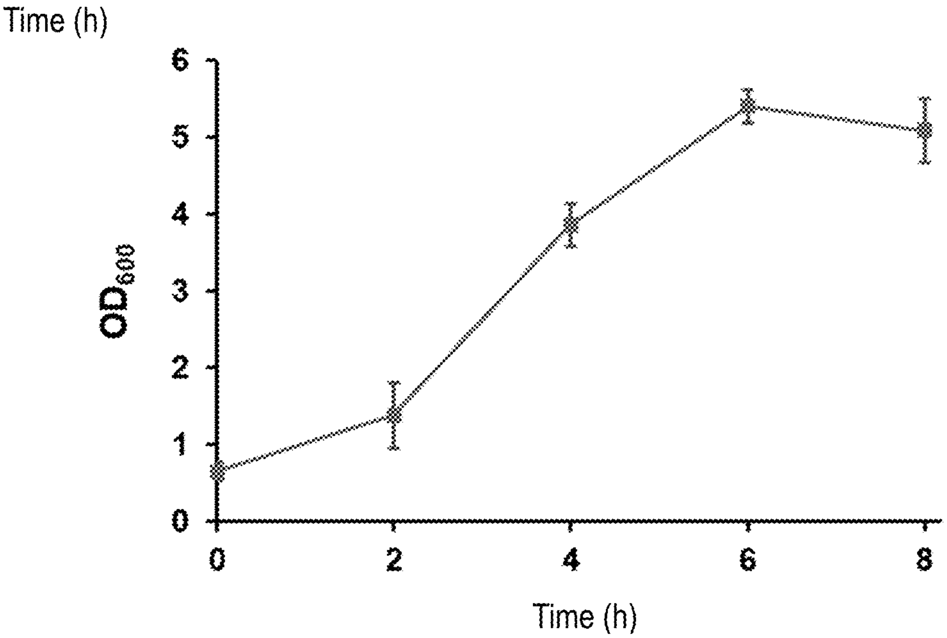
FIG. 4 shows a growth curve of *Bacillus subtilis* FNFH_BS08.

(3) The growth curve of *Bacillus subtilis* FNFH_BS08 in the LB liquid medium is shown in FIG. 4.

Meanwhile, the FNFH_BS08 strain has been preserved in the China General Microbiological Culture Collection Center (CGMCC for short, address: No. 3 Courtyard 1 West Beichen Road, Chaoyang District, Beijing, Institute of Microbiology, Chinese Academy of Sciences) on May 6, 2022, with a preservation number of CGMCC No. 24837.

Embodiment 3: Use of *Bacillus subtilis* FNFH_BS08 in Fermentation of Soybean Meal Experimental Materials:

Strain: *Bacillus subtilis* FNFH_BS08.

Mediums:

LB medium: 10 g/L peptone, 5 g/L yeast extract, 5 g/L sodium chloride;

GYP medium: 10 g/L glucose, 8 g/L yeast extract, 2 g/L soy peptone, pH 7.0.

Experimental Method:

1. Pre-treatment of soybean meal: 20 g of soybean meal was weighed and placed in a 250 mL sterilized shake flask whose opening was sealed with a gauze and a sealing film, high-pressure sterilization was carried out at 100° C. for 30 minutes, and cooling was then carried out to a room temperature.
2. Seed preparation: *Bacillus subtilis* FNFH_BS08 was inoculated onto a 6 mL LB medium and subjected to overnight activation culture at 37° C. and 250 rpm. Then the *Bacillus subtilis* FNFH_BS08 was transferred to a fresh 30 mL GYP medium with OD-0.5 and cultured at 37° C. and 250 rpm until the logarithmic growth phase.
3. Fermentation inoculation: the seed liquid of *Bacillus subtilis* FNFH_BS08 cultured until the logarithmic growth phase was mixed with a certain volume of sterile water at an inoculation amount of 3% (v./m.) (the total volume of a mixed seed liquid was 20 mL, even if the initial water content of soybean meal fermentation was 50%), 20 mL of the mixed seed liquid was evenly sprinkled into the pre-treated soybean meal and mixed thoroughly, and then the shake flask was placed in a constant-humidity shaking table for fermentation for 24 hours at 37° C. and 150 rpm.
4. Drying detection: after the fermentation was completed, the soybean meal was taken out and dried at 60° C., then crushed and sieved with a 60-mesh sieve, the contents of glycinin and β-conglycinin, the contents of a crude protein and a water-soluble protein, the degree of soybean meal protein degradation and the protein molecular weight distribution in the product fermented soybean meal obtained by fermentation and the raw material soybean meal were detected, respectively; the contents of ash, crude fiber, phosphorus, a trypsin inhibitor, stachyose and raffinose, and the number of live *Bacillus subtilis* were detected.

The degradation rates of glycinin and β-conglycinin were calculated according to the formula, and the protein solubility was calculated according to the formula as follows: Protein solubility=Content of water-soluble protein/Content of crude protein×100%.

Content of glycinin: detected by using enzyme linked immunosorbent assay according to the product manual of a glycinin quantitative detection kit purchased from Beijing Longke Fangzhou Biological Engineering Technology Center;

Content of β-conglycinin: detected by using enzyme linked immunosorbent assay according to the product manual of a β-conglycinin quantitative detection kit purchased from Beijing Longke Fangzhou Biological Engineering Technology Center;

Content of crude protein: detected by using the Kjeldahl method (GB/T 6432-2018);

Content of water-soluble protein: 1 g of a sample was weighed and dissolved in 40 mL of double distilled water, subjected to vortex shake for 2 hours, and then centrifuged at 1500 rpm for 10 minutes to collect a supernatant, which was quantified according to the method for determining the content of crude protein, i.e., the Kjeldahl method (GB/T 6432-2018).

Degree of soybean meal protein degradation: 1 g of a sample was weighed and dissolved in 5 mL of an 8 M urea solution, subjected to vortex for 30 minutes, and then centrifuged at 4° C. at 8000 rpm for 5 minutes to separate a supernatant, which was quantified by using a BCA protein quantitative kit, the amount of sample application of the sample was calculated at the 30 μg of protein content, and then the sample was loaded onto polyacrylamide gel for SDS-PAGE analysis.

Protein molecular weight distribution: 1 g of a sample was weighed and dissolved in 5 mL of an 8 M urea solution, subjected to vortex for 30 minutes, and then centrifuged at 4° C. at 8000 rpm for 5 minutes to separate a supernatant, which was filtered by a 0.45 μm syringe filter and then detected by high performance size exclusion chromatography. A method is to derive the protein molecular weight distribution in the sample to be tested by analyzing standard proteins with different molecular weights to determine the retention time of each protein and then calculating the standard curve of the relationship between molecular weight and retention time. More specifically, after the retention time of proteins with specific molecular weights was calculated, the chromatogram was divided into several parts based on time, and the proportion of the partial area of each molecular weight range to the entire chromatogram area was calculated.

Content of ash: detected by using the ignition method (GB/T 6438-2007).

Content of crude fiber: detected by using the filtration method (GB/T 6434-2006).

Content of phosphorus: detected by using spectrophotometry (GB/T 6437-2018).

Stachyose and raffinose: detected by using high performance liquid chromatography (Appendix A in NY-T2218-2012).

Trypsin inhibitor: detected by using the spectrophotometer method (GB 5009.224-2016).

*Bacillus*: detected by using the method for food microbiology detection-aerobic plate count determination (GB 4789.2-2016).

Figure 5:
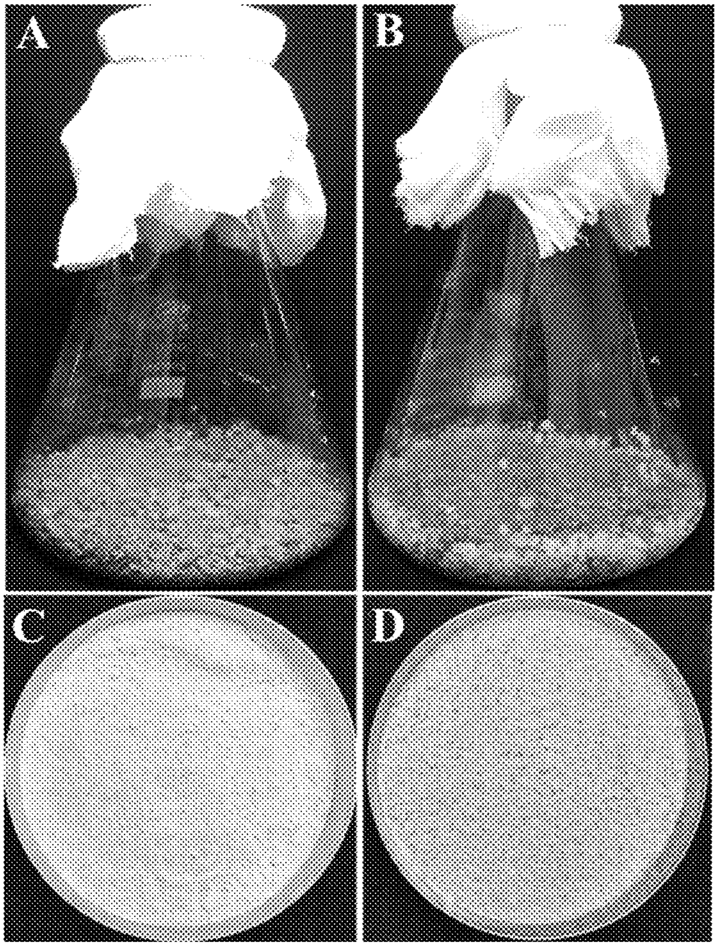
FIG. 5 shows pictures before and after fermentation of *Bacillus subtilis* FNFH_BS08, A: shake flask at 0 h of fermentation; B: shake flask at 24 h of fermentation; C: crushed soybean meal; D: crushed fermented soybean meal.

Experimental Results:

The product fermented soybean meal (FIG. 5) obtained by fermentation of the *Bacillus subtilis* FNFH_BS08 is a beige to golden yellow, without any odor, with a faint scent and sour flavor, and with soft, delicate and non-granular texture. This proves that the product fermented soybean meal obtained by fermentation of the *Bacillus subtilis* FNFH_BS08 has good sensory quality.

After the *Bacillus subtilis* FNFH_BS08 is applied to fermentation of soybean meal for 24 hours, the contents of the crude protein and water-soluble protein of the obtained product fermented soybean meal are significantly increased, while the content of the antigen proteins are significantly decreased (Table 3). The content of the crude protein was increased by 15.5%, the content of the water-soluble protein was increased by 687.9%, and the corresponding protein solubility was increased by 579.5%, while the degradation rates of the glycinin and β-conglycinin reached 92.2% and 85.1%, respectively. In addition, compared to the raw material soybean meal, the contents of anti-nutritional factors such as the stachyose, the raffinose and the trypsin inhibitor in the fermented soybean meal were significantly reduced by 97.2%, 95.1%, and 92.4%, respectively (Table 3). This proves that after the *Bacillus subtilis* FNFH_BS08 is used for fermentation of soybean meal, the overall nutritional parameters of the soybean meal are significantly improved, mainly manifested by a decrease in levels of anti-nutritional factors such as antigen proteins, oligosaccharides, and a trypsin inhibitor, as well as an upregulation in total protein, total fat content, and protein solubility in the soybean meal. Therefore, it helps to improve the protein digestion and utilization rate of soybean meal.

TABLE 3

Analysis of key components of soybean meal before and after fermentation of *Bacillus subtilis* FNFH_BS08

| Key components | Raw material soybean meal | Fermented soybean meal | Changed proportion |
|---|---|---|---|
| Crude protein, % | 52.58 | 60.73 | ↑15.5% |
| Water-soluble protein, % | 6.13 | 48.30 | ↑687.9% |
| Protein solubility, % | 11.7 | 79.5 | ↑579.5% |
| Glycinin, mg/g | 132.14 | 10.33 | ↓92.2% |
| β-Conglycinin, mg/g | 117.46 | 17.51 | ↓85.1% |
| Ash, % | 7.08 | 7.46 | |
| Crude fiber, % | 5.54 | 4.72 | |
| Crude fat, % | 2.33 | 2.75 | |
| Phosphorus, % | 0.54 | 0.56 | |
| Stachyose, % | 3.21 | 0.09 | ↓97.2% |
| Raffinose, % | 0.82 | 0.04 | ↓95.1% |
| Trypsin inhibitor, mg/g | 9.62 | 0.73 | ↓92.4% |
| *Bacillus*, CFU/g | 7 | $8.75 \times 10^7$ | |

Figure 6:
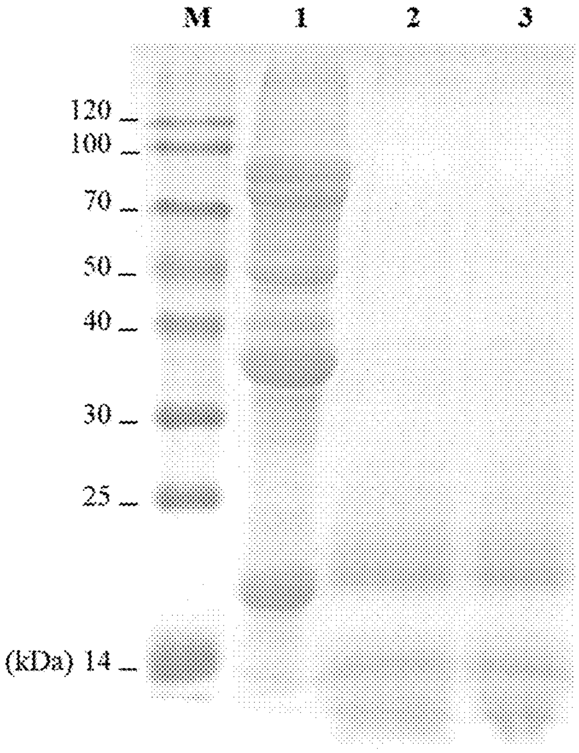
FIG. 6 shows a picture of results of protein detection by sodium dodecyl sulfate-polyacrylamide gel electrophoresis (SDS-PAGE).

The degree of total protein degradation before and after fermentation of soybean meal by *Bacillus subtilis* FNFH_BS08 is shown in FIG. 6. Compared with the raw material soybean meal, in the product fermented soybean meal obtained by fermentation of the *Bacillus subtilis FNFH_BS*08, the glycinin (30-45 kDa) and the β-conglycinin (50-100 kDa) are basically completely degraded, and the vast majority of macromolecular insoluble proteins in the soybean meal are degraded into micromolecular soluble proteins and peptides (<25 kDa).

Furthermore, the protein molecular weight distribution before and after fermentation of soybean meal by *Bacillus subtilis* FNFH_BS08 was detected by high performance size exclusion chromatography. The results are shown in Table 4. The raw material soybean meal contains about 85% of high molecular weight proteins and peptides with a molecular weight of 30 kDa or above. On the contrary, in the fermented soybean meal obtained by fermentation of *Bacillus subtilis FNFH_BS*08, the proportion of small molecular weight proteins and peptides of 30 kDa and below reaches about 82%. It is worth noting that the proportion of peptides less than 10 kDa in the fermented soybean meal reaches 43%. This proves that most of the high molecular weight proteins contained in soybean meal raw materials are hydrolyzed into low molecular weight peptides through fermentation, thereby improving the bioavailability of soybean meal proteins.

TABLE 4

Change in protein weight of soybean meal before and after fermentation of *Bacillus subtilis* FNFH_BS08

| Molecular weight (kDa) | Raw material soybean meal | Fermented soybean meal |
|---|---|---|
| >75 | 38.4% | 5.1% |
| 30-75 | 46.9% | 13.4% |
| 10-30 | 9.0% | 38.5% |
| <10 | 5.7% | 43.0% |
| Total | 100.0% | 100.0% |

```
>16S rRNA sequence with a full length of 1444 bp
                                          (SEQ ID NO: 1)
CATGGCTCAGGACGAACGCTGGCGGCGTGCCTAATACATGCAAGTCGAG

CGGACAGATGGGAGCTTGCTCCCTGATGTTAGCGGCGGACGGGTGAGTA

ACACGTGGGTAACCTGCCTGTAAGACTGGGATAACTCCGGGAAACCGGG

GCTAATACCGGATGGTTGTTTGAACCGCATGGTTCAGACATAAAAGGTG

GCTTCGGCTACCACTTACAGATGGACCCGCGGCGCATTAGCTAGTTGGT

GAGGTAACGGCTCACCAAGGCGACGATGCGTAGCCGACCTGAGAGGGTG

ATCGGCCACACTGGGACTGAGACACGGCCCAGACTCCTACGGGAGGCAG

CAGTAGGGAATCTTCCGCAATGGACGAAAGTCTGACGGAGCAACGCCGC

GTGAGTGATGAAGGTTTTCGGATCGTAAAGCTCTGTTGTTAGGGAAGAA

CAAGTGCCGTTCAAATAGGGCGGCACCTTGACGGTACCTAACCAGAAAG

CCACGGCTAACTACGTGCCAGCAGCCGCGGTAATACGTAGGTGGCAAGC

GTTGTCCGGAATTATTGGGCGTAAAGGGCTCGCAGGCGGTTTCTTAAGT

CTGATGTGAAAGCCCCCGGCTCAACCGGGGAGGGTCATTGGAAACTGGG

GAACTTGAGTGCAGAAGAGGAGAGTGGAATTCCACGTGTAGCGGTGAAA

TGCGTAGAGATGTGGAGGAACACCAGTGGCGAAGGCGACTCTCTGGTCT

GTAACTGACGCTGAGGAGCGAAAGCGTGGGGAGCGAACAGGATTAGATA

CCCTGGTAGTCCACGCCGTAAACGATGAGTGCTAAGTGTTAGGGGGTTT

CCGCCCCTTAGTGCTGCAGCTAACGCATTAAGCACTCCGCCTGGGGAGT

ACGGTCGCAAGACTGAAACTCAAAGGAATTGACGGGGGCCCGCACAAGC

GGTGGAGCATGTGGTTTAATTCGAAGCAACGCGAAGAACCTTACCAGGT
```

-continued

CTTGACATCCTCTGACAATCCTAGAGATAGGACGTCCCCTTCGGGGGCA

GAGTGACAGGTGGTGCATGGTTGTCGTCAGCTCGTGTCGTGAGATGTTG

GGTTAAGTCCCGCAACGAGCGCAACCCTTGATCTTAGTTGCCAGCATTC

AGTTGGGCACTCTAAGGTGACTGCCGGTGACAAACCGGAGGAAGGTGGG

GATGACGTCAAATCATCATGCCCCTTATGACCTGGGCTACACACGTGCT

ACAATGGACAGAACAAAGGGCAGCGAAACCGCGAGGTTAAGCCAATCCC

ACAAATCTGTTCTCAGTTCGGATCGCAGTCTGCAACTCGACTGCGTGAA

GCTGGAATCGCTAGTAATCGCGGATCAGCATGCCGCGGTGAATACGTTC

CCGGGCCTTGTACACACCGCCCGTCACACCACGAGAGTTTGTAACACCC

GAAGTCGGTGAGGTAACCTTTTA

>gyrB sequence 1004 bp (SEQ ID NO: 2)

ACCGCCAAACTTATAAACGCGGAGTTCCGGTTACAGACCTTGAAATCAT

TGGCGAAACGGATCATACAGGAACGACGACACATTTTGTCCCGGACCCT

GAAATTTTCTCAGAAACAACCGAGTATGATTATGATCTGCTTGCCAACC

GCGTACGTGAATTAGCCTTTTTAACAAAGGGCGTAAACATCACGATTGA

GGATAAACGTGAAGGACAAGAGCGCAAAAATGAATACCATTACGAAGGC

-continued

GGAATTAAAAGTTATGTAGAGTATTTAAACCGTTCTAAAGAGGTTGTCC

ATGAAGAGCCGATTTACATTGAAGGCGAAAAGGACGGCATAACGGTTGA

AGTAGCTTTGCAATACAATGACAGCTACACAAGCAACATTTACTCGTTT

ACAAACAACATTAACACGTACGAAGGCGGTACCCATGAAGCTGGCTTTA

AAACGGGCCTGACTCGTGTTATCAACGATTACGCCAGAAAAAAAGGGCT

TATTAAAGAAAATGATCCAAACCTAAGCGGAGATGACGTAAGGGAAGGG

CTGACAGCGATTATTTCAATCAAACACCCTGATCCGCAGTTTGAGGGCC

AAACGAAAACAAAGCTGGGCAACTCAGAAGCACGGACGATCACCGATAC

GTTATTTTCTGCGGCGATGGAAACATTTATGCTGGAAAATCCAGATGCG

GCCAAAAAAATTGTCGATAAAGGCTTAATGGCGGCAAGAGCAAGAATGG

GGGTGACTCTGCCGGAGGATCTGCTAAACAAGGACGCGACAGACATTTC

CCTGCGAAAAAAGCGCGTGAACTAACACGCCGTAAGAGTGCTTTGGAAA

TTTCAAACCTGCCCGGTAAGTTAGCGGACTGCTCTTCAAAAGATCCGAG

CATCTCCGAGTTATATATCGTAGAAAGCCATTTTGCCGCTTAGAGGTAA

GATCCTAAACGTTGAAAAGGCCAGACTGGATAAAATCCTTTCTAACAAC

GAAGTTCGCTCTATGATCACAGCG

What is claimed is:

1. A *Bacillus subtilis* FNFH_BS08, with a preservation number of CGMCC No. 24837.

2. A method of degrading antigen proteins and/or non-starch polysaccharides, comprising:

adding the *Bacillus subtilis* FNFH_BS08 of claim 1 to a substrate containing the antigen proteins and/or non-starch polysaccharides.

3. The method of claim 2, wherein the antigen proteins comprise glycinin and β-conglycinin, and the non-starch polysaccharides comprise cellulose, xylan, mannan, and pectin.

4. A method of fermenting soybean meal, comprising:

adding the *Bacillus subtilis* FNFH_BS08 of claim 1 to the soybean meal.

5. A method of improving a nutritional value of soybean meal in fermentation of the soybean meal, comprising:

adding the *Bacillus subtilis* FNFH_BS08 of claim 1 to the soybean meal, wherein the improving a nutritional value of soybean meal is specifically manifested by a decrease in content of antigen proteins, non-starch polysaccharides, oligosaccharides and a trypsin inhibitor, an increase in content of a crude protein and a water-soluble protein, and an increase in protein solubility in fermented soybean meal.

* * * * *

SEQUENCE LISTING

```
Sequence total quantity: 2
SEQ ID NO: 1           moltype = RNA  length = 1444
FEATURE                Location/Qualifiers
source                 1..1444
                       mol_type = genomic RNA
                       organism = Bacillus subtilis
SEQUENCE: 1
catggctcag gacgaacgct ggcggcgtgc ctaatacatg caagtcgagc ggacagatgg  60
gagcttgctc cctgatgtta gcggcggacg ggtgagtaac acgtgggtaa cctgcctgta  120
agactgggat aactccggga aaccggggct aataccggat ggttgtttga accgcatggt  180
tcagacataa aaggtggctt cggctaccac ttacagatgg acccgcggcg cattagctag  240
ttggtgaggt aacggctcac caaggcgacg atgcgtagcc gacctgagag ggtgatcggc  300
cacactggga ctgagacacg gcccagactc ctacgggagg cagcagtagg gaatcttccg  360
caatggacga aagtctgacg gagcaacgcc gcgtgagtga tgaaggtttt cggatcgtaa  420
agctctgttg ttagggaaga acaagtgccg ttcaaatagg gcggcacctt gacggtacct  480
aaccagaaag ccacggctaa ctacgtgcca gcagccgcgg taatacgtag gtggcaagcg  540
ttgtccggaa ttattgggcg taaagggctc gcaggcggtt tcttaagtct gatgtgaaag  600
cccccggctc aaccggggag ggtcattgga aactggggaa cttgagtgca gaagaggaga  660
gtggaattcc acgtgtagcg gtgaaatgcg tagagatgtg gaggaacacc agtggcgaag  720
gcgactctct ggtctgtaac tgacgctgag gagcgaaagc gtggggagcg aacaggatta  780
gataccctgg tagtccacgc cgtaaacgat gagtgctaag tgttaggggg tttccgcccc  840
ttagtgctgc agctaacgca ttaagcactc cgcctgggga gtacggtcgc aagactgaaa  900
ctcaaaggaa ttgacggggg cccgcacaag cggtggagca tgtggtttaa ttcgaagcaa  960
cgcgaagaac cttaccaggt cttgacatcc tctgacaatc ctagagatag gacgtcccct  1020
tcgggggcag agtgacaggt ggtgcatggt tgtcgtcagc tcgtgtcgtg agatgttggg  1080
ttaagtcccg caacgagcgc aacccttgat cttagttgcc agcattcagt tgggcactct  1140
aaggtgactg ccggtgacaa accggaggaa ggtggggatg acgtcaaatc atcatgcccc  1200
ttatgacctg ggctacacac gtgctacaat ggacagaaca aagggcagcg aaaccgcgag  1260
gttaagccaa tcccacaaat ctgttctcag ttcggatcgc agtctgcaac tcgactgcgt  1320
gaagctggaa tcgctagtaa tcgcggatca gcatgccgcg gtgaatacgt tcccgggcct  1380
tgtacacacc gcccgtcaca ccacgagagt ttgtaacacc cgaagtcggt gaggtaacct  1440
ttta                                                               1444

SEQ ID NO: 2           moltype = DNA  length = 1004
FEATURE                Location/Qualifiers
source                 1..1004
                       mol_type = genomic DNA
                       organism = Bacillus subtilis
SEQUENCE: 2
accgccaaac ttataaacgc ggagttccgg ttacagacct tgaaatcatt ggcgaaacgg  60
atcatacagg aacgacgaca cattttgtcc cggaccctga aattttctca gaaacaaccg  120
agtatgatta tgatctgctt gccaaccgcg tacgtgaatt agccttttta acaaagggcg  180
```

-continued

```
taaacatcac gattgaggat aaacgtgaag gacaagagcg caaaaatgaa taccattacg  240
aaggcggaat taaaagttat gtagagtatt taaaccgttc taaagaggtt gtccatgaag  300
agccgattta cattgaaggc gaaaaggacg gcataacggt tgaagtagct ttgcaataca  360
atgacagcta cacaagcaac atttactcgt ttacaaacaa cattaacacg tacgaaggcg  420
gtacccatga agctggcttt aaaacgggcc tgactcgtgt tatcaacgat tacgccagaa  480
aaaaagggct tattaaagaa aatgatccaa acctaagcgg agatgacgta agggaagggc  540
tgacagcgat tatttcaatc aaacaccctg atccgcagtt tgagggccaa acgaaaacaa  600
agctgggcaa ctcagaagca cggacgatca ccgatacgtt attttctgcg gcgatggaaa  660
catttatgct ggaaaatcca gatgcggcca aaaaaattgt cgataaaggc ttaatggcgg  720
caagagcaag aatggctgcg aaaaaagcgc gtgaactaac acgccgtaag agtgctttgg  780
aaatttcaaa cctgcccggt aagttagcgg actgctcttc aaaagatccg agcatctccg  840
agttatatat cgtagagggt gactctgccg gaggatctgc taaacaagga cgcgacagac  900
atttccaagc cattttgccg cttagaggta agatcctaaa cgttgaaaag gccagactgg  960
ataaaatcct ttctaacaac gaagttcgct ctatgatcac agcg                 1004
```